US006194208B1

(12) United States Patent
Belford et al.

(10) Patent No.: US 6,194,208 B1
(45) Date of Patent: *Feb. 27, 2001

(54) MODIFIED MILK GROWTH FACTOR

(75) Inventors: David Andrew Belford, Seacliff Park; Mary-Louise Rogers, North Adelaide; Geoffrey Owen Regester, Ferntree Gully; Geoffrey Welsford Smithers, Cheltenham; Francis John Ballard, Kensington; Geoffrey Leonard Francis, Athelstone, all of (AU)

(73) Assignee: Gropep Limited, Adelaide South Austrialia (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,409

(22) PCT Filed: Apr. 26, 1995

(86) PCT No.: PCT/AU95/00237

§ 371 Date: Sep. 30, 1996

§ 102(e) Date: Sep. 30, 1996

(87) PCT Pub. No.: WO95/29933

PCT Pub. Date: Nov. 9, 1995

(30) Foreign Application Priority Data

Apr. 28, 1994 (AU) .................................................. PM 5347

(51) Int. Cl.[7] .................................................. A61K 38/43
(52) U.S. Cl. .......................... 435/391; 426/656; 435/325; 514/2; 530/350; 530/412
(58) Field of Search ............................ 426/656; 530/350, 530/412; 514/2; 435/244, 325, 391

(56) References Cited

U.S. PATENT DOCUMENTS

| 4,440,860 | | 4/1984 | Klagsbran | 435/240 |
| 4,520,036 | * | 5/1985 | Rialland et al. | 426/271 |
| 5,221,734 | * | 6/1993 | Burk et al. | 530/399 |
| 5,281,582 | * | 1/1994 | Dehazya | 514/21 |
| 6,010,698 | | 1/2000 | Kussendrager et al. | |

FOREIGN PATENT DOCUMENTS

| 62-86986 | | 3/1987 | (AU) . |
| 1952192 | | 2/1993 | (AU) . |
| 0 313 515 | * | 1/1987 | (EP) . |
| 0313515 | | 4/1989 | (EP) . |
| 0367447 | | 9/1990 | (EP) . |
| 0 527 283 A1 | * | 2/1993 | (EP) . |
| 3236772 | * | 10/1991 | (JP) . |
| WO 92/00994 | * | 1/1992 | (WO) . |
| 9308264 | | 4/1993 | (WO) . |
| 9320713 | | 10/1993 | (WO) . |

OTHER PUBLICATIONS

S.M. Donovan et al. "Growth Factors in Milk . . . " Annu. Rev. Nutr. 14:147–67 (1994).
D. Watson et al. "Factors in Ruminant . . . " Journal of Dairy Research, vol. 59 (1992) 59 369–380.
F.A. Simmen et al. "Maternal and Neonatal . . . " Developmental Biology 130, 16–27 (1988).
N. Azuma et al. "Occurrence of High Molecular . . . " Agric. Biol. Chem. 53 (4) 1043–1050. 1989.
D. Cox et al. "Isolation and Characterisation . . . " Eur. J. Biochem. 197, 353–358 (1991).
G. L. Francis et al. "Insulin–like growth factors . . . " Biochem. J. (1988) 251. 95–103.
T. Kanda et al. "Growth Factor From Human Milk . . . " Life Sciences, vol. 55, No. 19 pp. 1509–1520 (1994).
S. Saito et al. "Transforming growth factor–Beta" Clin. Exp. Immunol 1993: 94:220–224, 1994.
C.E. Grosvenor et al. "Hormones and Growth . . . " Endocrine Reviews, vol. 14, 710 (1992).
Chemical Abstracts, vol. 119, Abstract 146574N. "Osteoblast growth factor . . . ".
Damerdji et al. (1988) Biotechnology Techniques vol. 2, No. 4, pp. 253–258 [Reference H of IDS].*
Saito et al. (1993) Clin. Exp. Immunol., vol. 94, pp. 220–224.*
Sullivan et al. (1983) J. Chromatog., vol. 266, pp. 301–311.*
Shetty et al. (1992) Biol. Neonate, vol. 62, pp. 409–415.*
Dai et al. (1985) Pediatric Res., vol. 19, No. 9, pp. 916–918.*
Klagsbrun, M. "Human Milk Stimulates DNA . . . " Proc. Natl. Acad. Sci. USA vol. 75, No. 10, pp. 5057–5061 (1978).
Klagsbrun, M. "The Serum–Free Growth . . . " J. Supramol. Struct. 11, 349 (1979) 229–239.
Klagsbrun, M. "Bovine Colostrum Supports . . . " J. Cell. Biol. 88, 294 (1981) pp. 808–814.

(List continued on next page.)

Primary Examiner—Leon B. Lankford, Jr.
(74) Attorney, Agent, or Firm—Ladas & Parry

(57) ABSTRACT

The invention provides a process for preparing a plurality of modified milk growth factors which process includes: providing a milk product extract including a plurality of milk growth factors having basic to approximately neutral isoelectric points and a source of acid; subjecting the milk product extract to transient acidification utilising the acid source; and isolating a plurality of modified milk growth factors from the transiently acidified milk product extract. Also provided are growth promoting compositions, cell culture compositions, and pharmaceutical or veterinary compositions for the treatment of surface wounds, gastrointestinal injuries, diseases or ulcers, each including a plurality of modified milk growth factors having isoelectric points above approximately 6.0 and molecular weights in the range of approximately 5000 to 30.000, the milk growth factors being modified by transient acidification.

27 Claims, 6 Drawing Sheets

OTHER PUBLICATIONS

Steimer et al. "Serum–free Growth of Normal . . . " J. Cell Biol. 88, 294 (1981) pp. 294–300.

Sereni, A. et al. "Routine Growth of Cell lines . . . " Cell Biology International Reports, vol. 5, No. 4, Apr. (1981).

A. Knar, "The Serum–free Growth of Different . . . " Experimentia, 39, 534 (1983) pp. 534–535.

Derouiche et al. "Biochemical Aspects of a Whey . . . " Lait 70, pp. 313–324 (1990).

Damerdji et al. "Utilisation of Whey . . . " Biotechnology Techiques vol. 2, No. 4, pp. 253–258 (1988).

Ichiba, H. et al. "Measurement of Growth Promoting . . . " Biol. Neonate. 61. 47 (1992).

Pakkaren, R. et al. "Bovine Colostrum Fraction . . . " Appl. Microbiol Biotechol. (1992) 37:451–456.

Japanese Patent Abstract (in English) DBA Accession No. 8500965 for JP 59166079, (1984).

* cited by examiner

MODIFIED MILK GROWTH FACTOR

This invention relates to the modification of growth factors in milk or milk extracts and to improved methods for the extraction of such growth factors from milk or milk products and their use in cell culture and pharmaceutical applications.

Animal cells are grown in culture to provide a number of pharmaceutical, diagnostic and veterinary products including human vaccines, lymphokines, hormones, monoclonal antibodies, other pharmaceutically active protein products, veterinary hormones and for research and development and diagnostic purposes.

The growth of animal cells requires a defined isotonic medium that contains salts, nutrients, lipid precursors, nucleic acid precursors, vitamins and amino acids that are formulated to mimic the medium that would normally bathe those cells in vivo. Examples in common use include Eagle's Minimal Essential Medium, Dulbecco's modified Eagle's Minimal Essential Medium (DMEM), Medium 199, RPMI 1640 medium and Ham's F12 Medium. However, virtually no animal cells will grow in such media, but require the co-addition of serum. Fetal bovine serum is frequently used as it is more effective than serum obtained from post-natal animals and it contains only minimal concentrations of immunoglobulins which otherwise could have undesirable effects.

The supply of fetal bovine serum is limited by the number of pregnant cows slaughtered. It also has undesirable lot-to-lot variations and may include toxins. Particular concern surrounds its use for the eventual production of recombinant proteins and other pharmaceuticals for human use because the serum may also contain viruses that are harmful to humans and may be carried through a purification protocol that yields the desired product. Principally for these reasons, extensive efforts have been directed towards the replacement of serum by pure ingredients. Examples of such ingredients are growth factors, hormones and cell attachment factors. Unfortunately, the requirements of each cell type being grown are different and are difficult to establish. Frequently it has not proved possible to achieve equivalent growth properties or equivalent yields of cell products with "serum-free" media as can be obtained with medium containing fetal bovine serum.

The limited availability of fetal bovine serum, its lot-to-lot variability, its resultant considerable cost as well as the deficiencies of "serum-free" media described above have prompted the investigation of other biological fluids as potential replacements in cell culture media. Some progress has been reported in the prior art with bovine milk and bovine colostrum as evidenced by the following selected reports: M. Klagsbrun, Proc. Natl. Acad. Sci. USA 75, 5057 (1978); M. Klagsbrun et al. J. Supramol. Struct. 11, 349 (1979); M. Klagsbrun, J. Cell Biol. 84, 808 (1980); K. S. Steimer et al. J. Cell Biol. 88, 294 (1981); A. Sereni et al. Cell Biol. Intl. Rep. 5, 339 (1981); A. Khar Experientia 39, 534 (1983); O. Damerdji et al. Biotech. Tech. 2, 253 (1988); O. T. Ramirez et al. Lait 70, 313 (1990); H. Ichiba et al. Biol. Neonate. 61, 47 (1992); R. Pakkanen et al. Appl. Microbiol. Biotechnol. 37, 451 (1992). These and other publications alluded to herein are incorporated by reference.

The prior art also includes U.S. Pat. No. 4,440,860 to M. Klagsbrun which describes "compositions and methods for promoting cell growth featuring, in one aspect, cell culture media containing milk or colostrum and fibronectin; fibronectin is preferably pre-coated onto the culture substrate" and Japan Patent JP 59166879 to Morinaga "A culture medium for cell incubation—containing milk or milk components". Ultrafiltrates of milk whey have also been used to support the growth of cultured cells, as in European Patent A0219372 to G. Linden et al. "Fractions de lait, Procedee d'obtention de ces fractions et milleux de culturo cellulaires renfermant ces fractions" and application WO 90106357 to G. Linden et al. "Supplements of animal cell culture media based on products derived from the milk industry". An active fraction from colostrum obtained by hydroxyapatite chromatography has been reported in application WO 92/00014 by B. Quinque et al. "Method for treating colostrum thereby obtained, and a cellular medium containing same" and by cation exchange chromatography in Australian Patent 645589 to F. J. Ballard et al. "Growth-promoting agent". The prior art also includes Australian Patent 598205 to F. J. Ballard et al. "Growth Factor" and European Patent 03 13515 to R. R. Burk et al. "A polypeptide growth factor from milk" in which individual growth factors have been isolated from colostrum or milk in pure form.

This progress has led to the development of formulations that support the growth of some cell types but usually require protein concentrations in the medium that approach those in more general use with fetal bovine serum.

It is accordingly an object of the present invention to overcome or at least alleviate one or more of the deficiencies related to the prior art.

According to the present invention there is provided a process for preparing a plurality of modified milk growth factors which process includes providing
   a milk product extract including
      a plurality of milk growth factors having basic to approximately neutral isoelectric points; and
      a source of acid,
   subjecting the milk product extract to transient acidification utilising the acid source; and
   isolating a plurality of modified milk growth factors from the transiently acidified milk product extract.

Preferably the isolation step includes subjecting the transiently acidified milk product extract to a purification step to remove inactive proteins.

By "transient acidification" is meant acidification for a period sufficient to enhance the growth promoting activity of the factors whilst avoiding any significant degradation of the factors.

The present invention further provides a growth promoting composition exhibiting enhanced growth stimulating activity including a plurality of modified milk growth factors having isoelectric points above approximately 6.0 and molecular weights in the range of approximately 5000 to 30,000, the milk growth factors being modified by transient acidification.

Preferably the modified milk growth factors have isoelectric points between approximately 6.0 and 10.5.

The team "milk" as used herein refers to lactational secretions of human or animal origin.

The term "modified milk growth factor" as used herein refers to growth factors of milk that exhibit enhanced growth promoting activity compared to the growth promoting activity of the same growth factors in their occurring state or when extracted from milk, a milk product or a milk product extract.

The term "milk product" as used herein refers to a derivative from human or animal milk in which the fat and/or protein constituents thereof are reduced. Examples of milk product include milk whey, skim milk, cheese whey and acid (casein) whey. Preferably the milk product is cheese whey.

The term "milk product extract" as used herein refers to an extract of milk product in which the salt and/or main protein constituents thereof are reduced. Examples of milk product extracts are ultrafiltrates of milk products or milk products that have been subjected to adsorption and to elution from chromatography matrices. Preferably the milk product extract is cheese whey that has been subjected to cation exchange chromatography by the method described in Australian Patent 645,589.

Preferably the modified growth factor are obtained by acidifying milk product extract containing growth factors having basic to approximately neutral isoelectric points. Preferably inactive proteins are removed from the modified milk growth factors in accordance with the invention. Molecular sieve chromatography or ultrafiltration under acidic conditions may be used to remove inactive proteins. Molecular sieve chromatography is particularly preferred as it removes higher molecular weight proteins such as growth factor binding proteins that would otherwise recombine with certain growth factors after transient acidification.

The term "enhanced growth promoting activity" as used herein is a measure of increased cellular growth per unit of growth factor compared to the growth promoting activity of the same growth factors in their occurring state or when extracted from milk, a milk product or a milk product extract. Preferably cellular growth per unit of growth factor is increased by 10%, more preferably by 25%.

Accordingly, in a preferred aspect, the purification step in the process of the present invention includes subjecting the transiently acidified milk product extract to a chromatography or ultrafiltration process performed under acidic conditions, preferably performed at a pH of approximately 3.0 or below.

Preferably the chromatography process is a molecular sieve chromatography process and the ultrafiltration process is a controlled pore ultrafiltration process. Preferably the controlled pore ultrafiltration is performed using a membrane that excludes molecules larger than approximately 100 kDa, more preferably approximately 50 kDa, most preferably approximately 30 kDa.

In a further preferred aspect, the process of the present invention further provides the preliminary step of providing a source of milk or milk product;

a cationic exchange resin; and a buffer solution;

contacting the milk or milk product with the cation exchange resin such that the more basic components of the milk or milk product are absorbed thereon;

eluting the cationic exchange resin with the buffer solution; and collecting a milk product extract therefrom.

The preliminary purification step is more fully described in Australian Patent 645,589 to applicants.

Preferably the milk product extract includes a GFE-2 or like growth promoting agent as hereinafter defined.

Preferably the growth factors are subject to acidification to a pH of approximately 3.0 or below. More preferably the factors are acidified to a pH in the range 2.0 to 3.0. An acidification pH of about 2.5 is particularly preferred.

Preferably acidification is carried out using an inorganic acid, for example, HCl. For example acidification may be achieved by dissolving the milk product extract in water and acidifying with a strong inorganic acid such as 5M HCl and drying. Preferably the growth stimulating factors in the milk product extract are obtained by carrying out cation exchange chromatography on a milk product. The milk product extract may be produced by the method described in Australian Patent Application 645,589.

As stated above, the process of the invention may include the further step of removing inactive proteins after acidification has taken place.

Removal of inactive proteins may be carried out using molecular sieve chromatography or ultrafiltration under acidic conditions. As mentioned previously, molecular sieve chromatography is particularly preferred as it removes high molecular weight proteins that would otherwise recombine with certain growth factors following neutralisation.

The present invention will be more fully described with reference to the milk product extract described in Applicant's earlier Australian application Patent 645,589 (herein incorporated by reference). However, this is illustrative only and should not be taken as a restriction on the generality of the invention.

The milk product extract used in the method of the invention should not previously have been subjected to transient acidification to approximately pH 3.0 or below.

The individual growth factors present in serum, milk or other biological fluids such as epidermal growth factor, insulin-like growth factor I or II, acidic or basic fibroblast growth factor, transforming growth factor alpha or beta, or platelet derived growth factor are all small proteins with molecular weights between 5,000 and 30,000. It was surprising, therefore, that following molecular sieve chromatography under conditions near neutral pH of the growth promoting agent GFE-2 described in Australian patent 645589 to F. J. Ballard et al., essentially all the cell growth stimulating activity was present in the high molecular weight region. Specifically, the growth promoting activity on L6 myoblasts, Balb/C 3T3 fibroblasts and human skin fibroblasts co-eluted with lactoperoxidase, the most abundant protein in GFE-2, which has a molecular weight of 78,000 (see FIG. 1, dashed line).

By the term "GFE-2 or like growth promoting agent" as used herein we mean a milk product extract in which a plurality of growth factors having neutral to basic isoelectric points are present and have been isolated as a milk growth factor extract by cation exchange chromatography without exposure to acidic conditions.

The unexpected finding that the growth promoting activity in GFE-2 extracted from cheese whey has a much higher molecular weight than essentially all known growth factors suggested that the growth effects in the GFE-2 were either elicited by unknown factors or by known factors but which were in the form of aggregates. The invention describes two approaches utilised to distinguish between these alternatives and provides methods for activating or enhancing the growth promoting activity of milk product extracts, and in particular enhancing the growth promoting activity of GFE-2 or like growth promoting agents.

In plasma, certain growth factors, for example insulin-like growth factors I and II, occur predominantly in association in binding protein complexes that include an acid-labile subunit (R. C. Baxter et al. Progress in Growth Factor Research 1, 49, 1989). Transient acidification of plasma releases the insulin-like growth factors to lower molecular weight forms that may have enhanced activities.

A similar process is known to release transforming growth factor beta from a high molecular weight complex (M. B. Sporn et al. J. Cell Biol. 105, 1039, 1987). Applicant has now found that if the growth factors in milk products such as cheese whey remain in complexes through the cation exchange chromatography step required to produce milk product extracts such as GFE-2, then transient acidification releases those factors and hence leads to an increase in the capacity of the milk extract to stimulate the growth of cultured cells. This is confirmed in the experiment shown in Example 2 where the growth of CHO-K1 cells is stimulated at much lower protein concentrations and to a greater extent with transiently acidified GFE-2 than with GFE-2 itself.

Accordingly there is provided in a preferred embodiment a plurality of modified milk product growth factors exhibiting enhanced growth stimulating activity and having isoelectric points above approximately 6.0 and molecular weights in the range of approximately 5000 to 30,000, the milk growth factors being modified by transient acidification.

Preferably the plurality of modified milk growth factors is modified GFE-2 or like growth promoting agent.

Whereas transient acidification does lead to enhanced growth-promoting activity in CHO-Kd1 cells, the total protein concentration of GFE-2 is not markedly reduced by such a process. The protein content of the acidified growth promoting extract may be substantially reduced by molecular sieve chromatography under acid conditions whereby the growth promoting activities are separated from the bulk of the inactive protein. Although the examples in FIGS. 3, 4 and 5 utilise Superose 12 HR 10/30™ (Pharmacia) and Matrex Cellufine GCL 1000™ (Amicon) molecular sieve column packings, these are illustrative only so that a person familiar with the art would recognise that similar separations could be obtained with other molecular sieve column packings.

In this embodiment of the invention the growth-promoting activity on several cell lines is transferred to the lower molecular weight region and separated from the bulk of extraneous proteins in GFE-2 (see FIG. 3). Should the individual fractions collected in the example of FIG. 3 instead be collected as a single molecular weight pool, as in example FIG. 4, the resultant pool exhibits growth-promoting activity at substantially lower protein concentrations than obtained with unfractionated GFE-2 (see FIG. 5).

In a further aspect of the invention the protein concentration of the acidified growth promoting extract may be reduced by controlled pore ultrafiltration instead of molecular sieve chromatography. When this is accomplished under acidic conditions using an ultrafiltration membrane with a nominal size cut off of, say, 100 kDa, the growth promoting activities may be transferred to the permeate as demonstrated in FIG. 6. Moreover, growth promoting activities occur at substantially lower protein concentrations than in unfractionated GFE-2. This example of use with a 100 kDa membrane is illustrative only so that a person familiar with the art would recognise that similar separations could be obtained with other membranes that allow passage of growth factors into the permeate fraction but retard the permeation of proteins with molecular weights larger than approximately 30,000.

In a further aspect the present invention provides a cell culture composition including an effective amount of a growth promoting composition exhibiting enhanced growth stimulating activity including a plurality of modified milk growth factors having isoelectric points above approximately 6.0 and molecular weights in the range of approximately 5000 to 30,000, the milk growth factors being modified by transient acidification; and a culture medium.

Preferably the plurality of modified milk growth factors is a modified GFE-2 or like growth promoting agent.

More preferably, the culture medium is a substantially protein-free culture medium and/or contains fetal bovine serum.

The present invention also provides a method for culturing human or animal cells which method includes providing a source of animal cells; and a cell culture composition including an effective amount of a growth promoting composition exhibiting enhanced growth stimulating activity including a plurality of modified milk growth factors having isoelectric points above approximately 6.0 and molecular weights in the range of approximately 5000 to 30,000, the milk growth factors being modified by transient acidification; and a culture medium; and culturing the cells in the cell culture composition for a time sufficient and at a temperature sufficient to achieve a predetermined cell concentration.

Preferably the cells are cultured at a temperature in the range of approximately 35° C. to 40° C. for a period of approximately 1 to 5 days.

The processes of this invention that include either transient acidification of milk product or acidification followed by separation to yield a low molecular weight fraction under acid conditions also can be applied to yield products for uses not restricted to the growth of cells in culture. In this context specific examples include growth of more organised structures in culture, such as skin for subsequent transplant to burned individuals or to cover exposed wounds.

The present invention also provides a pharmaceutical or veterinary composition for the treatment of surface wounds, which composition includes a plurality of modified milk growth factors having isoelectric points above approximately 6.0 and molecular weights in the range of approximately 5000 to 30,000, the milk growth factors being modified by transient acidification; and a pharmaceutically or veterinarily acceptable diluent, carrier or excipient therefor.

Preferably the composition further includes an effective amount of at least one active ingredient selected from antibiotics, antiseptics, other growth promotants, and mixtures thereof.

Accordingly the present invention provides a method of treating surface wounds in animals, including humans, which method includes administering to the patient to be treated an effective amount of a pharmaceutical or veterinary composition, which composition includes a plurality of modified milk growth factors having isoelectric points above approximately 6.0 and molecular weights in the range of approximately 5000 to 30,000, the milk growth factors being modified by transient acidification; and a pharmaceutically or veterinarily acceptable diluent, carrier or excipient therefor.

Preferably the composition further includes an effective amount of at least one active ingredient selected from antibiotics, antiseptics, other growth promotants, anaesthetics, and mixtures thereof.

The pharmaceutical or veterinary compositions may be adapted for the treatment of gastrointestinal injuries, diseases or ulcers. Accordingly the present invention provides a pharmaceutical or veterinary composition for the treatment of gastrointestinal injuries, diseases or ulcers, which composition includes a plurality of modified milk growth factors having isoelectric points above approximately 6.0 and molecular weights in the range of approximately 5000 to 30,000, the milk growth factors being modified by transient acidification; and a pharmaceutically or veterinarily acceptable diluent, carrier or excipient therefor.

Preferably the composition further includes an effective amount of at least one active ingredient selected from antibiotics, antiseptics, other growth promotants, anaesthetics, and mixtures thereof.

The present invention further provides a method for the treatment of a human or animal subject, said method including administering an effective amount of a growth promoting composition in accordance with the invention.

An application of this invention is to produce products that can be added directly to surface wounds where the enhanced growth-promoting activities can accelerate the repair of those wounds.

EXAMPLES

The present invention will now be more fully described with respect to the following examples. It should be understood, however, that the description following is illustrative only, and should not be taken in any way as a restriction of the generality of the invention described above.

EXAMPLE 1

Molecular sieve Chromatography of whey extract under Neutral pH Conditions Demonstrates cell Growth Promoting Activity Predominantly in the high Molecular Weight Region GFE-2 was prepared as in Australian Patent 645589 to F. J. Ballard et al. This process involved microfiltration of pasteurised whey to remove solids; adsorption of growth-promoting material to a column of S-Sepharose Fast Flow S™ cation exchange resin (Pharmacia) that had been equilibrated with 50 mM sodium citrate buffer at pH 6.5; washing the column with the same buffer to remove unadsorbed material; elution of GFE-2 with 0.4 M NaCl added to 10 mM sodium citrate pH 6.5; diafiltration against water, concentration by ultrafiltration and freeze drying.

The GFE-2 was dissolved in Dulbecco's phosphate buffered saline at pH 7.4 (PBS), passed through a 0.22 $\mu$m filter and 200 $\mu$l applied to a Superose 12 HR 10/30™ (Pharmacia) column equilibrated with the same buffer and chromatographed at 0.3 ml/min. Fractions of 0.9 ml were collected into tubes containing 100 $\mu$l of 10 mg bovine serum albumin/ml.

This example utilises the cell lines L6 (rat myoblast), Balb/C 3T3 (mouse fibroblast) and SF 1972 (human diploid skin fibroblast) to test the activities of each fraction.

Each cell line was subcultured on to 96-place tissue culture plates in Dulbecco-Modified Eagle's Minimal Essential Medium (DMEM) containing 10% fetal bovine serum (5% for L6 myoblasts) and left in a 5% $CO_2$, 37° C., humidified incubator overnight to ensure attachment of the cells. Sterile techniques were used throughout. The plates were thoroughly washed in DMEM to remove any residual serum and the whey fractions or fetal bovine serum (FBS) added at the indicated concentrations. The total volume in each well was 0.1 ml at 37° C., 5% $CO_2$ and 100% humidity.

Figure 1A:
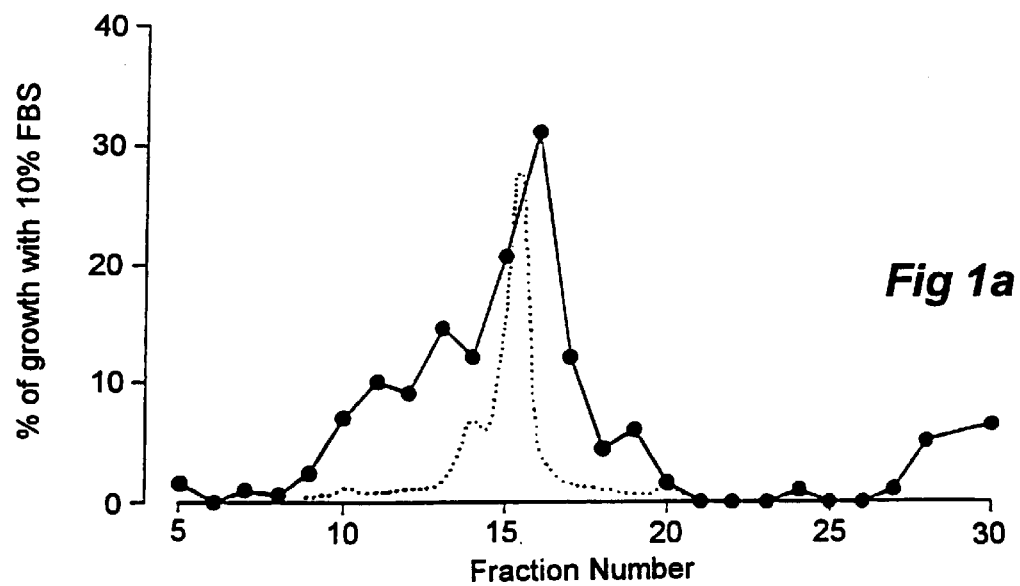
FIG. 1: Milk product extract GFE-2 as in Example 1 was dissolved in phosphate buffered saline and chromatographed on a Superose 12 HR10/30™ (Pharmacia) column equilibrated with the same buffer. Protein was measured by absorbance at 280 nm (dashed line). Growth promoting activity in each fraction was measured in the 3 cell lines [L6 Myoblasts (FIG. 1A), Balbd/C 3T3 (FIG. 1B), SF1972 (FIG. 1C)] as the percentage of growth achieved when 10% fetal bovine serum was the reference source of growth factor (●).
Figure 1B:
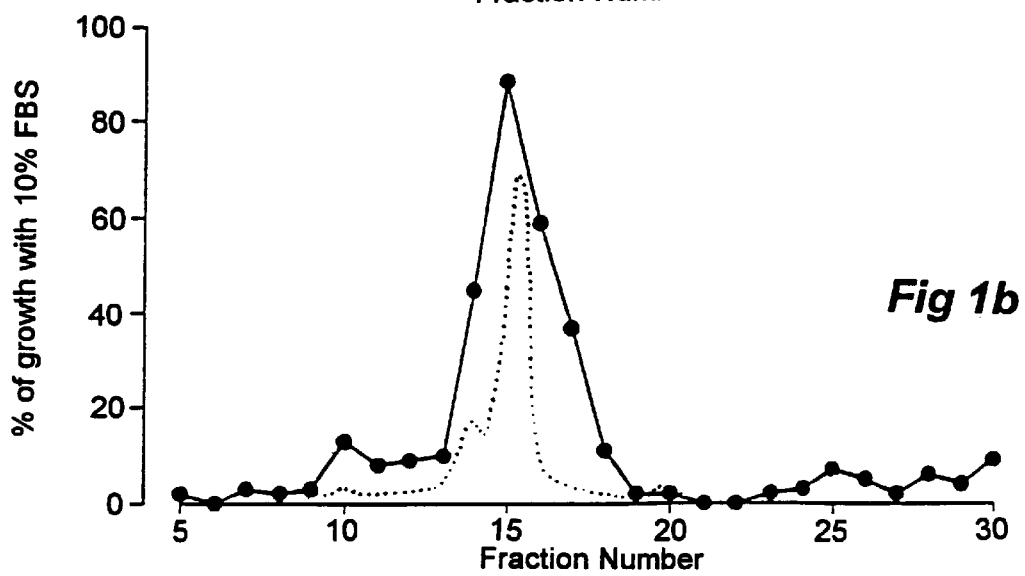
Figure 1C:
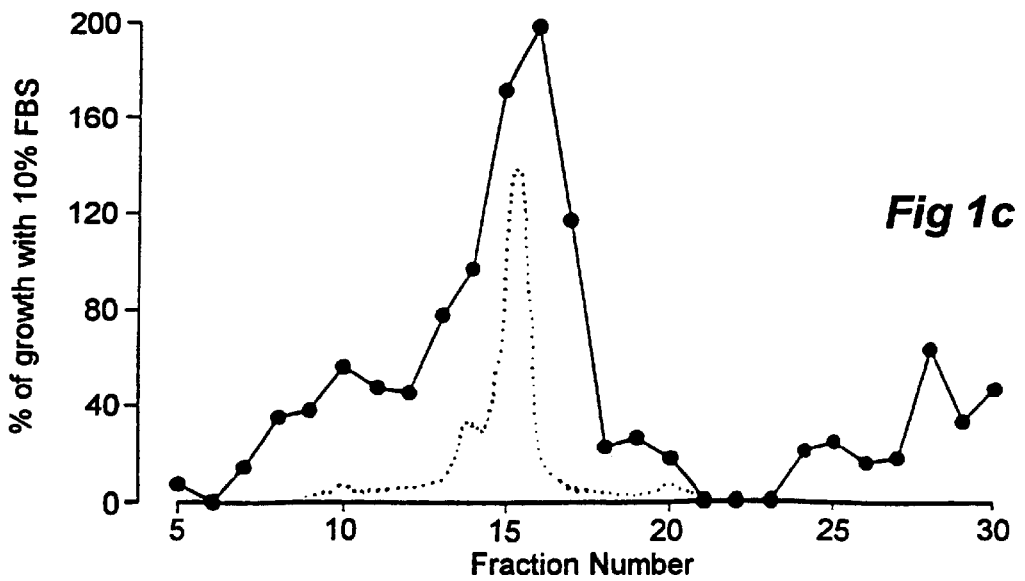

After a further 2 days the plates were washed, fixed and the cell numbers quantified using an automated methylene blue method (M. H. Oliver et al., J. Cell Sci. 92, 513, 1989). Growth is expressed as the percentage increase in absorbance units relative to the increase in absorbance produced by growing the cells in DMEM containing 10% fetal bovine serum (FIG. 1).

This example shows that in all three cell lines fetal bovine serum and 20 $\mu$l portions of certain fractions obtained from the column stimulated growth. The fractions with the most activity coincided with the main protein region eluted from the column as shown by its absorbance at 280 nm (dotted lines, FIG. 1). Activities in FIG. 1 are expressed as the percentage increase in growth relative to that obtained with 10% fetal bovine serum.

EXAMPLE 2

Transient Acidification Leads to Enhanced Growth Promoting Activity in CHO-K1 Cells A 50 mg sample of GFE-2 prepared as in Example 1 was dissolved in 2 ml of water and acidified to pH 1.6 with 5M HCl; adjusted to pH 2.5 with 0.5M NaOH and dried under vacuum. The dried material was dissolved in 1 ml of Ham's F12 cell culture medium containing 10 mg of bovine serum albumin and serially diluted in the same medium. A sample of GFE-2 at the same initial concentration and fetal bovine serum were similarly diluted in Ham's F12 medium containing bovine serum albumin.

The test solutions were evaluated for growth-promoting activity as described in Example 1 except that the cells were CHO-K1 and the medium Ham's F12 instead of DMEM.

Figure 2:
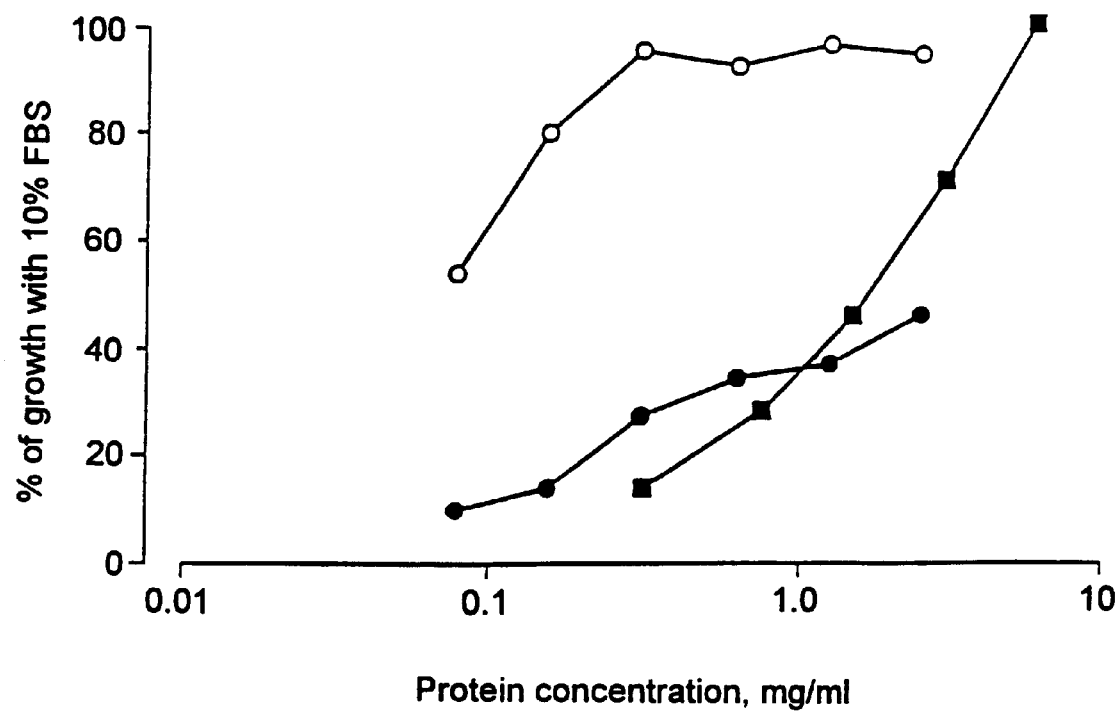
FIG. 2: Growth promoting activity in CHO-K1 cells by milk product extract GFE-2 as in Example 1 (●) and transiently acidified milk product extract GFE-2 prepared as in Example 2(○). Fetal bovine serum (FBS) is shown as a reference source of growth factors (■).

This example (FIG. 2) shows that whereas GFE-2 does produce a modest growth effect, much greater growth at lower total protein concentrations is achieved by the transiently acidified preparation.

Figure 3A:
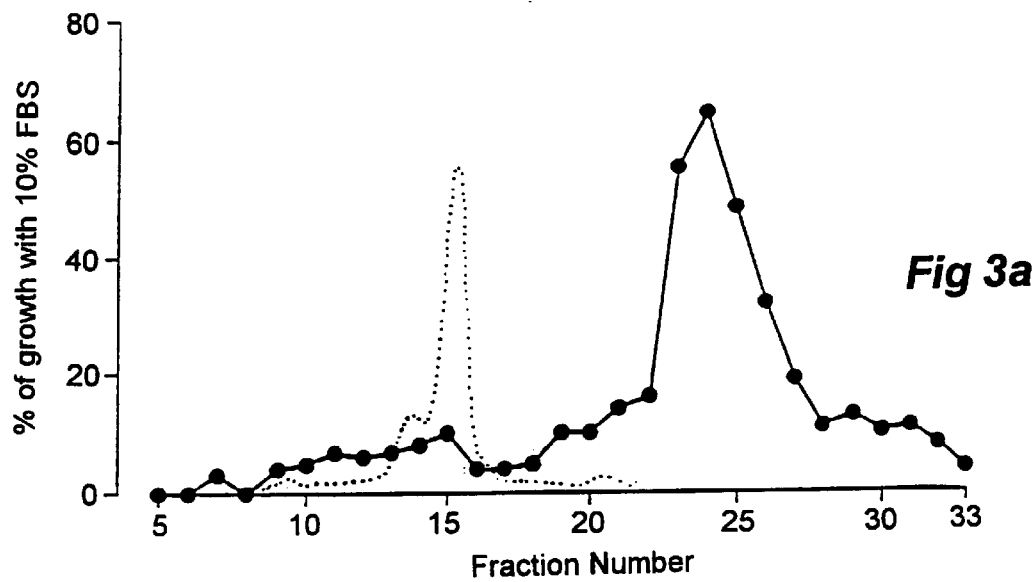
FIG. 3: Milk product extract GFE-2 as in Example 1 was acidified and subjected to molecular sieve chromatography as in Example 3. Protein is shown by its absorbance at 280 nm (dashed line). Growth promoting activity of dried and reconstituted fractions was measured in the 3 cell lines [L6 Myoblasts (FIG. 3A), Balb/C 3T3 (FIG. 3B), SF1972 (FIG. 3C)] as the percentage of growth achieved when 10% fetal bovine serum was the reference source of growth factors (●).
Figure 3B:
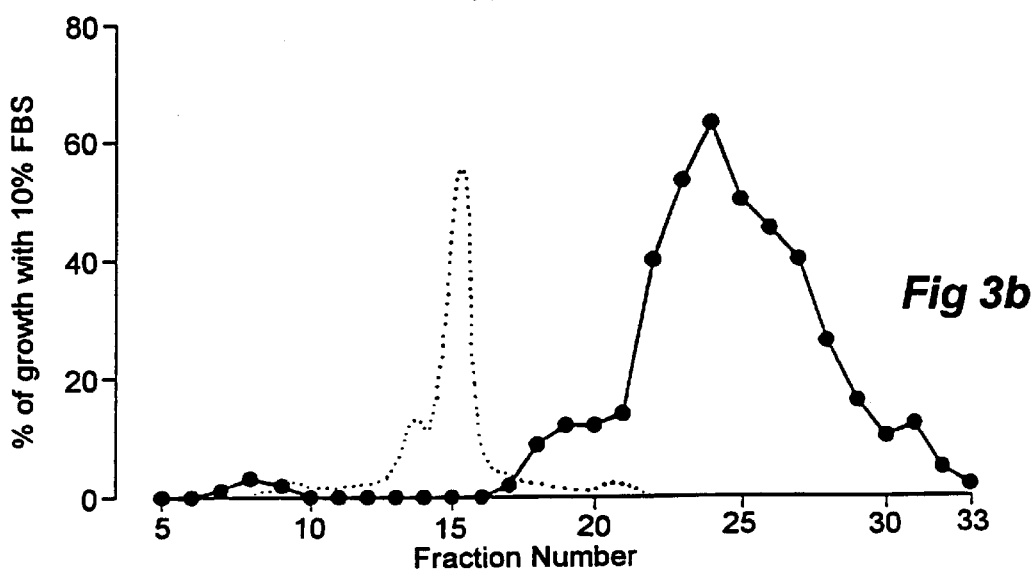
Figure 3C:
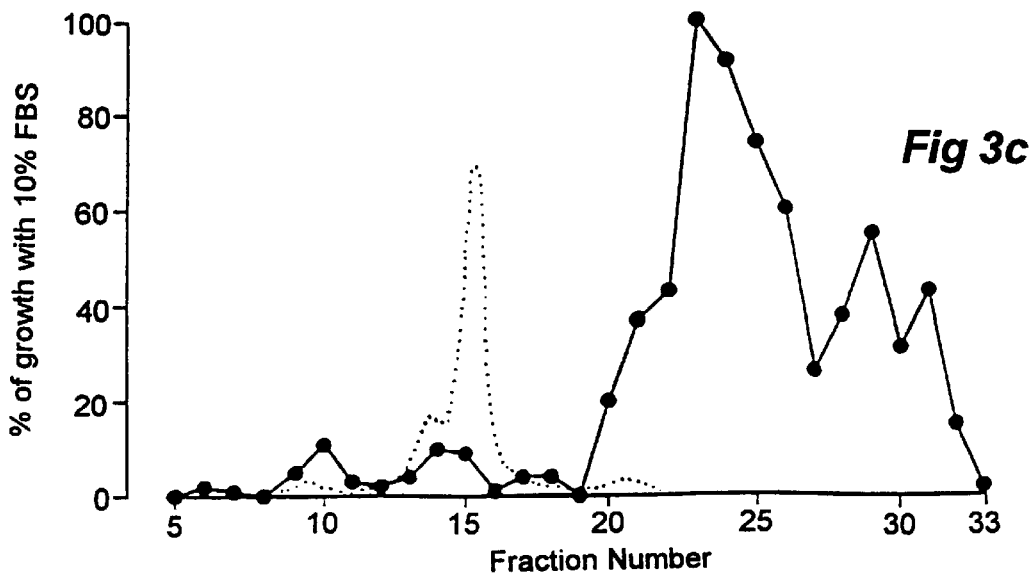

EXAMPLE 3
Molecular Sieve Chromatography under Acid Conditions Transfers the Growth Promoting Activity of Whey Extracts to the Low Molecular Weight Region GFE-2 was prepared as in Example 1. A 25 mg portion was dissolved in 1 M acetic acid containing 0.15M NaCl, passed through a 0.22 μm filter and 200 μl applied to the same Superose 12 HR 10/30 column as in Example 1 except that the column was equilibrated with 1M acetic acid containing 0.15M NaCl. Chromatography and sample collection were as described in Example 1 except that the elution buffer was 1M acetic acid containing 0.15M NaCl. The fractions were dried under vacuum, dissolved in DMEM and the growth promoting activities evaluated as described in Example 1. The results are shown in FIG. 3 with the protein absorbance profile shown as dotted lines.

This experiment showed that acidification of GFE-2 followed by molecular sieve chromatography led to the growth promoting activity in L6 myoblasts, Balb/C 3T3 and SF 1972 cells shifting to later elution volumes than the protein absorbance peak; hence to low molecular weight regions.

EXAMPLE 4
The Pooled Low Molecular Weight Fraction Obtained after Molecular Sieve Chromatography of Whey Extracts Under acid Conditions has Enhanced Specific Activity for Supporting Cell Growth.

Figure 4:
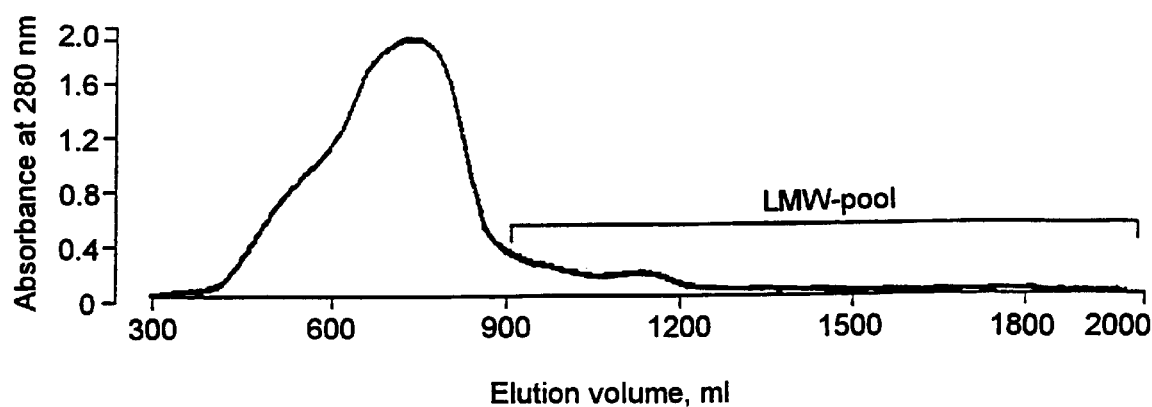
FIG. 4: Larger scale preparation of a modified milk growth factor by chromatography of acidified GFE-2 on Matrex Cellufine GCL 1000™ (Amicon) under acid conditions according to Example 4. The low molecular weight pool (LMW-pool) was collected and dried for subsequent assay of growth promoting activity.

GFE-2 was prepared as in Example 1. A 10 g portion was dissolved in 250 ml of 10 mM HCl containing 0.2M NaCl and the pH adjusted to 2.5 with NaOH. This solution was used to equilibrate a 2 litre Cellufine GCL 1000™ (Amicon) column. 125 ml of the dissolved GFE-2 was applied to the column and eluted at 6.8 ml/min with the same solution. 675 ml was collected from when the absorbance profile at 280 nm fell below 0.4 (FIG. 4). This pool was diafiltered against 0.1 M ammonium bicarbonate and freeze-dried to yield 385 mg of product.

The low molecular weight pool (LMW pool) and GFE-2 were dissolved as described in Example 1 and cell growth measured as in that Example except that the cell lines tested were L6 myoblasts, SF 3169 human skin fibroblasts and human endothelial cells obtained as described by E. Jaffe et al. J. Clin. Invest 52, 2745 (1973).

Figure 5A:
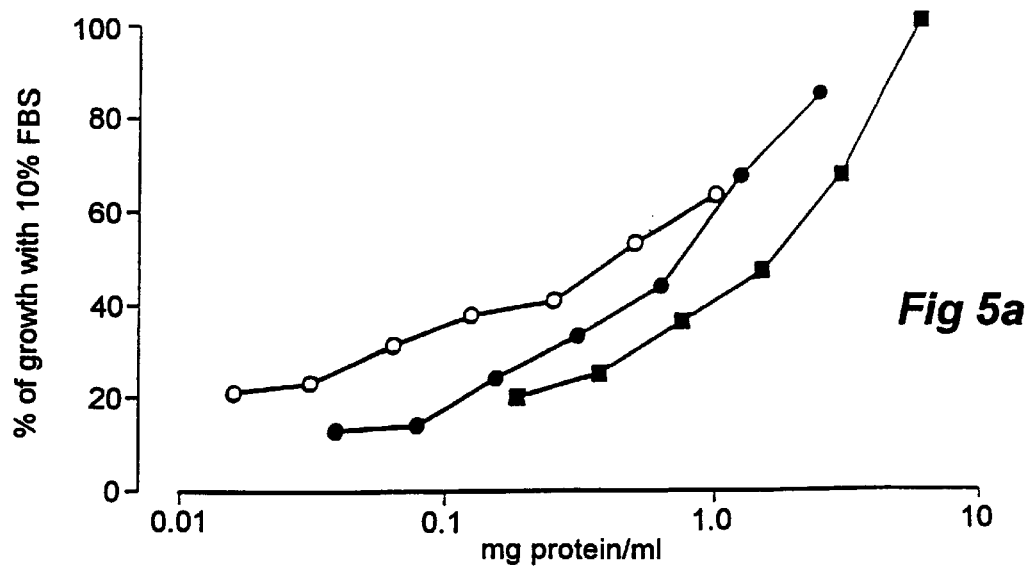
FIG. 5: Growth promoting activities of GFE-2 prepared as in Example 1 (●) and the LMW-pool prepared as in Example 4 (○) on 3 cell lines [L6 Myoblasts (FIG. 5A), human endothelial cells (FIG. 5B), SF3169 (FIG. 5C)]. Fetal bovine serum (FBS) is shown as a reference source of growth factors (■).
Figure 5B:
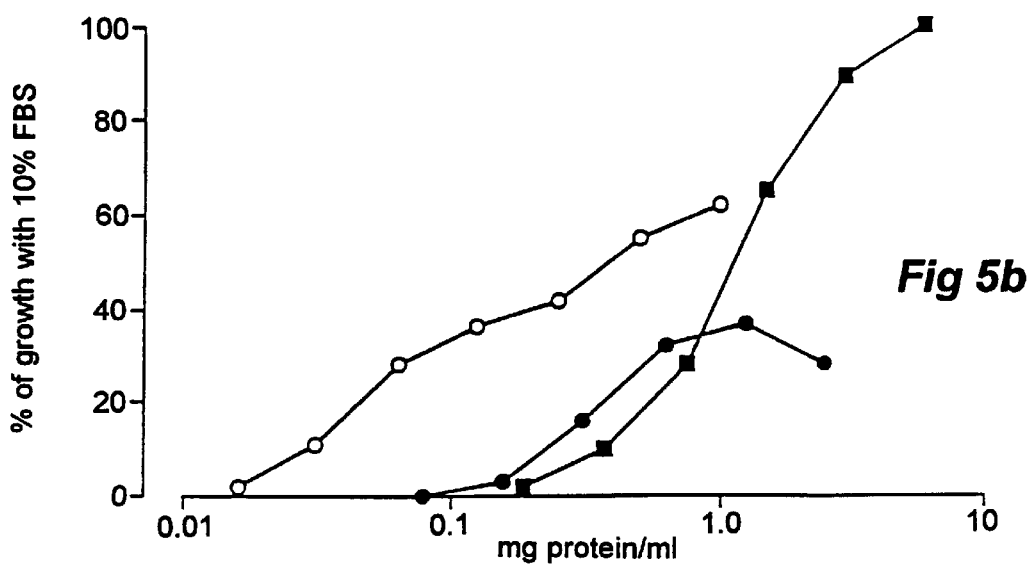
Figure 5C:
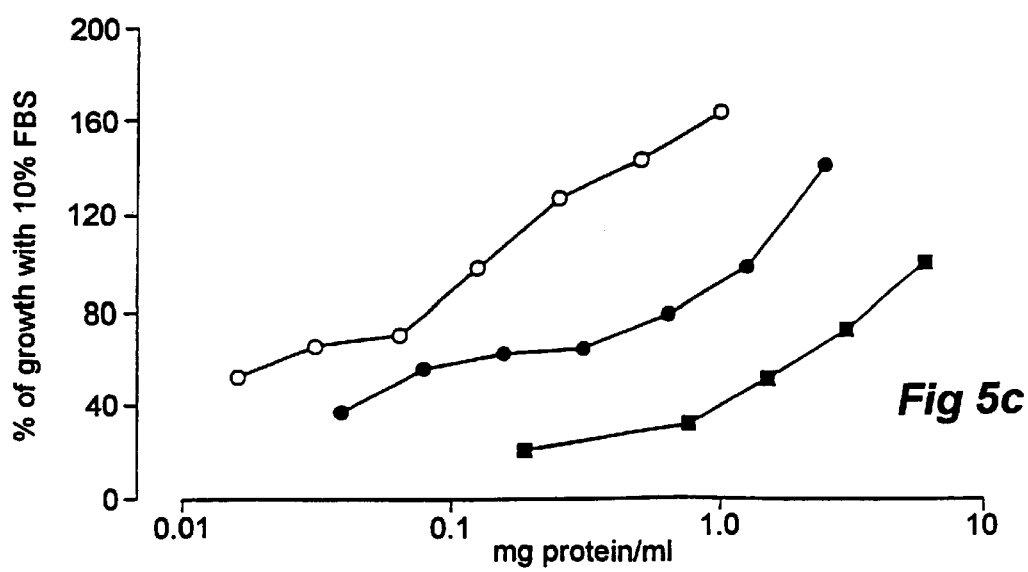

This experiment shows that lower concentrations of LMW pool stimulated growth than obtained with GFE-2. This increased specific activity was particularly apparent with the human skin fibroblast and human endothelial cells, as shown in FIG. 5.

EXAMPLE 5
Controlled Pore Ultrafiltration Under Acid Conditions Transfers the Growth Promoting Activity of Whey Extract to the Permeate.

GFE-2 was prepared as in Example 1. 40 g of GFE-2 was suspended in 40L of 10 mM tri-sodium citrate and adjusted to pH 2.5 using 0.1M HCl. The acidified protein solution was left overnight at 4° C. and then concentrated to 5L against a large pore ultrafiltration membrane (Sartorius, 0.7 m², polysulfone, 100kDa cut-off pore size). The concentrate was diafiltered extensively (20:1) with 100L of 150 mM NaCl/HCl solution at pH 2.5. Permeate (approx. 130L) collected from the concentration/diafiltration cycle was adjusted to pH 7.0 with 0.1M NaOH and transferred to an Amicon ultrafiltration system equipped with a single 1.8 m², spiral wound polysulfone membrane (3kDa cut-off pore size). The permeate was concentrated in this system to 10L; diafiltered (5:1) with 50L of 150 mM $NH_4HCO_3$, and then further concentrated to a final volume of 250 ml. The concentrated permeate was freeze dried, yielding approximately 1.8 g of powder.

Figure 6A:
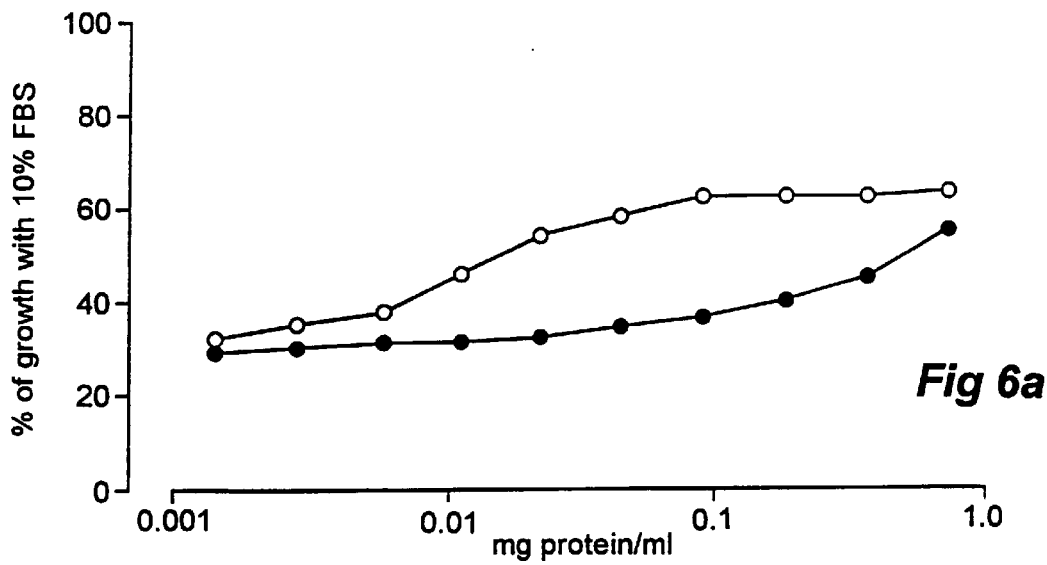
FIG. 6: Growth promoting activities of GFE-2 prepared as in Example 1 (●) and a permeate of acidified GFE-2 obtained by ultrafiltration through a 100 kDa membrane (Sartorius) (○) on 3 cell lines [L6 Myoblasts (FIG. 6A), Balb/C 3T3 (FIG. 6B), SF1967 (FIG. 6C)]. Activities are expressed relative to those achieved when 10% fetal bovine serum was the reference source of growth factors.
Figure 6B:
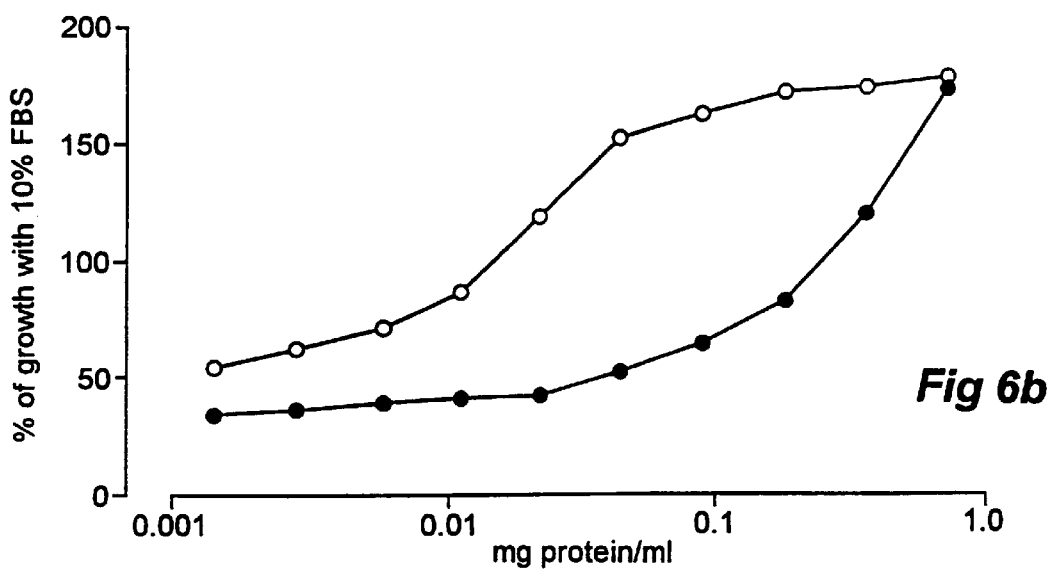
Figure 6C:
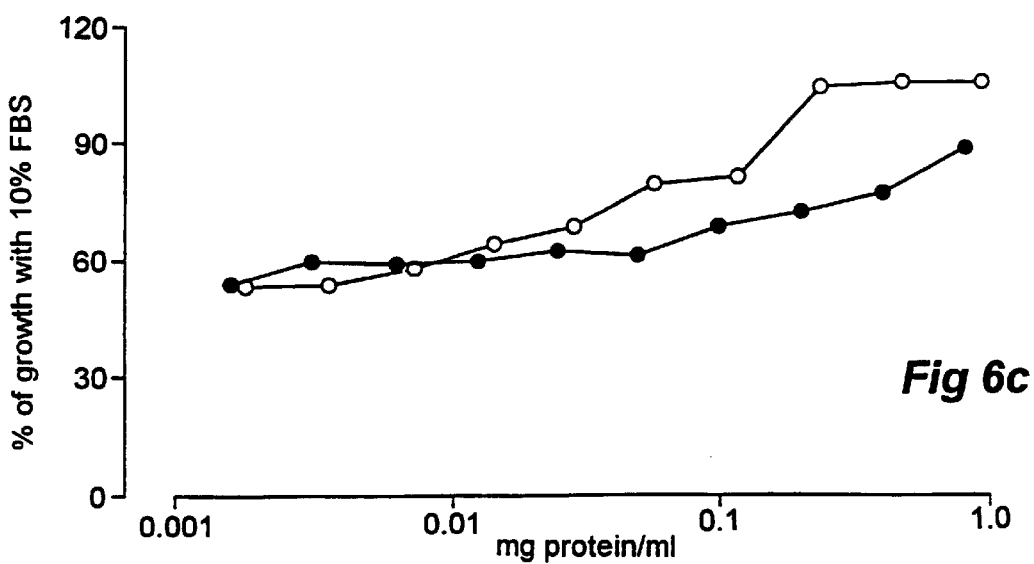

The dried permeate and GFE-2 were dissolved in water and the growth promoting activities evaluated as described in Example 1. The results are shown in FIG. 6.

This experiment shows that the permeate obtained through ultrafiltration of acidified whey extract supports the growth of L6 myoblasts, Balb/C 3T3 and SF 1967 cells, a human skin fibroblast line similar to the SF 1972 and SF 3169 cells used in Examples 1, 3 and 4. Furthermore, the growth promoting activity in all three cell lines occurs at substantially lower protein concentrations than observed with GFE-2.

Finally, it is to be understood that various other modifications and/or alterations may be made without departing from the spirit of the present invention as outlined herein.

What is claimed is:

1. A process for preparing a growth extract, which process comprises:
    (a) isolating a milk protein mixture from a milk product selected from the group consisting of cheese whey, skim milk, and casein whey, the isolated milk protein mixture comprising growth factors having a basic to approximately neutral isoelectric point, being enriched in growth promoting activity, and having the ability to stimulate proliferation of rat myoblasts, the milk protein mixture being isolated by ion exchange chromatography without exposure to acidic conditions such that the milk protein mixture elutes during the chromatography in a fraction having a high molecular weight; and
    (b) subjecting the isolated milk protein mixture to transient acidification with an acid source to obtain an acidified growth promoting extract with a cell growth promoting activity that is enhanced as compared with the cell growth promoting activity of the milk protein mixture isolated in step (a).

2. A process according to claim 1 wherein the isolated milk protein mixture is subjected to transient acidification to a pH of approximately 3.0 or below.

3. A process according to claim 1 wherein the milk product is cheese whey.

4. A process according to claim 1 further including subjecting the acidified growth promoting extract to a purification step under acidic conditions to remove inactive proteins.

5. A process according to claim 4 wherein the purification step includes subjecting the acidified growth promoting extract to a molecular sieve chromatography process to obtain milk growth factors having molecular weights in the range of approximately 5,000 to 30,000 Dalton.

6. A process according to claim 4 wherein the purification step includes a controlled pore ultrafiltration process using a membrane to obtain milk growth factors having molecular weights in the range of approximately 5,000 to 30,000 Dalton.

7. A process according to claim 1, wherein the faction in which the milk product mixture elutes during the chromatography has a molecular weight above 30,000 Dalton.

8. A process for preparing a growth extract, said process comprising:
    (a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
   filtering the milk product to remove insoluble material therefrom;
   adjusting the pH of the resulting ultrafiltrate to between approximately 6.5 and 8.0;
   equilibrating an agarose-based cation exchange resin with an equilibration buffer to provide a cation exchange resin suitable for adsorbing basic protein;
   applying the pH adjusted ultrafiltrate to the equilibrated cation exchange resin;
   eluting the cation exchange resin with a buffer suitable for such eluting and recovering an eluate comprising said growth factors in a fraction having a high molecular weight;
   filtering the eluate to reduce the salt content thereof;
   concentrating the filtered eluate to obtain the milk protein mixture enriched in growth promoting activity and having the ability to stimulate proliferation of rat myoblasts;
(b) providing a source of acid; and
(c) subjecting the milk protein mixture to transient acidification utilizing the acid source for a period sufficient to enhance the growth promoting activity of growth factors in the milk protein mixture so as to obtain an acidified growth promoting extract with a cell growth promoting activity that is enhanced as compared with the cell growth promoting activity of the milk protein mixture provided in step (a).

9. A process according to claim 8 wherein the milk protein mixture is subjected to transient acidification to a pH of approximately 3.0 or below.

10. A process according to claim 8 wherein the milk product is cheese whey.

11. A process according to claim 8 further including subjecting the acidified growth promoting extract to a purification step under acidic conditions to remove inactive proteins.

12. A process according to claim 11 wherein the purification step includes subjecting the acidified growth promoting extract to a molecular sieve chromatography process to obtain milk growth factors having molecular weights in the range of approximately 5,000 to 30,000 Dalton.

13. A process according to claim 11 wherein the purification step includes a controlled pore ultrafiltration process using a membrane to obtain milk growth factors having molecular weights in the range of approximately 5,000 to 30,000 Dalton.

14. A process for preparing a cell culture composition, said process including:
   (a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
      1) filtering the milk product to remove solid material therefrom:
      2) contacting the product thereof with an equilibrated cation exchange resin to adsorb the more basic components of the mixture and then eluting the resin with a buffer solution and recovering an eluate comprising said growth factors in a fraction having a high molecular weight;
      3) diafiltration of the eluate against water; and
      4) concentrating the filtered eluate to obtain the milk protein mixture enriched in growth promoting activity and having the ability to stimulate proliferation of rat myoblasts; and
   (b) providing a source of acid;
   (c) providing a culture medium; and
   (d) subjecting the milk protein mixture to transient acidification utilizing the acid source for a period sufficient to enhance the growth promoting activity of growth factors in the milk protein mixture so as to obtain an acidified growth promoting extract with a cell growth promoting activity that is enhanced as compared with the cell growth promoting activity of the milk protein mixture provided in step (a); and
   combining said acidified growth promoting extract with the culture medium.

15. A process according to claim 14 wherein the culture medium is a substantially protein free culture medium.

16. A process for preparing a cell culture composition, said process including:
   (a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
      filtering the milk product to remove insoluble material therefrom;
      adjusting the pH of the resulting ultrafiltrate to between approximately 6.5 and 8.0;
      equilibrating an agarose-based cation exchange resin with an
      equilibration buffer to provide a cation exchange resin suitable for adsorbing basic protein;
      applying the pH adjusted ultrafiltrate to the equilibrated cation exchange resin;
      eluting the cation exchange resin with a buffer suitable for such eluting and recovering an eluate comprising said growth factors in a fraction having a high molecular weight;
      filtering the eluate to reduce the salt content thereof;
      concentrating the filtered eluate to obtain the milk protein mixture enriched in growth promoting activity and having the ability to stimulate proliferation of rat myoblasts;
   (b) providing a source of acid;
   (c) providing a culture medium; and
   (d) subjecting the milk protein mixture to transient acidification utilizing the acid source for a period sufficient to enhance the growth promoting activity of growth factors in the milk protein mixture so as to obtain an acidified growth promoting extract with a cell growth promoting activity that is enhanced as compared with the cell growth promoting activity of the milk protein mixture provided in step (a); and
   combining said acidified growth promoting extract with said culture medium.

17. A process according to claim 16 wherein the culture medium is a substantially protein free culture medium.

18. A method of culturing human and animal cells which method includes:
(i) preparing a cell culture composition by a process including:
  (a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
    1) filtering the milk product to remove solid material therefrom;
    2) contacting the product thereof with an equilibrated cation exchange resin to adsorb the more basic components of the mixture and then eluting the resin with a buffer solution and recovering an eluate comprising said growth factors in a fraction having a high molecular weight;
    3) diafiltration of the eluate against water; and
    4) concentrating the filtered eluate to obtain the milk protein mixture enriched in growth promoting activity and having the ability to stimulate proliferation of rat myoblasts; and
  b) providing a source of acid;
  c) providing a culture medium; and
(ii) subjecting the milk protein mixture to transient acidification utilizing the acid source for a period sufficient to enhance the growth promoting activity of growth factors in the milk protein mixture to obtain an acidified growth promoting extract with a cell growth promoting activity that is enhanced as compared with the cell growth promoting activity of the milk protein mixture provided in step i(a); and
(iii) combining said acidified growth promoting extract with the culture medium and
(iv) culturing the cells in the cell culture composition for a time sufficient and at a temperature sufficient to achieve a predetermined cell concentration.

19. A method of culturing human and animal cells which method includes:
(i) preparing a cell culture composition by a process including:
  (a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
    filtering the milk product to remove insoluble material therefrom;
    adjusting the pH of the resulting ultrafiltrate to between approximately 6.5 and 8.0;
    equilibrating an agarose-based cation exchange resin with an equilibration buffer to provide a cation exchange resin suitable for adsorbing basic protein;
    applying the pH adjusted ultrafiltrate to the equilibrated cation exchange resin;
    eluting the cation exchange resin with a buffer suitable for such
    eluting and recovering an eluate comprising said growth factors in a fraction having a high molecular weight;
    filtering the eluate to reduce the salt content thereof;
    concentrating the filtered eluate to obtain the milk protein mixture enriched in growth promoting activity and having the ability to stimulate proliferation of rat myoblasts;
  (b) providing a source of acid;
  (c) providing a culture medium; and
  (d) subjecting the milk protein mixture to transient acidification utilizing the acid source for a period sufficient to enhance the growth promoting activity of growth factors in the milk protein mixture so as to obtain an acidified growth promoting extract with a cell growth promoting activity that is enhanced as compared with the cell growth promoting activity of the milk protein mixture provided in step (a); and
  (e) combining said acidified growth promoting extract with said culture medium; and
  (f) culturing the cells in the cell culture composition for a time sufficient and at a temperature sufficient to achieve a predetermined cell concentration.

20. A process for preparing a pharmaceutical or veterinary composition for the treatment of surface wounds, said process includes:
(a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
  1) filtering the milk product to remove solid material therefrom;
  2) contacting the product thereof with an equilibrated cation exchange resin to adsorb the more basic components of the mixture and then eluting the resin with a buffer solution and recovering an eluate comprising said growth factors in a fraction having a high molecular weight;
  3) diafiltration of the eluate against water; and
  4) concentrating the filtered eluate to obtain the milk protein mixture enriched in growth promoting activity and having the ability to stimulate proliferation of rat myoblasts;
b) providing a source of acid;
c) providing a pharmaceutically or veterinary acceptable diluent, carrier or excipient therefore
  (d) subjecting the milk protein mixture to transient acidification utilizing the acid source for a period sufficient to enhance the growth promoting activity of growth factors in the milk protein mixture to obtain an acidified growth promoting extract with a cell growth promoting activity that is enhanced as compared with the cell growth promoting activity of the milk protein mixture provided in step (a); and
  (e) combining said acidified growth promoting extract with the pharmaceutically or veterinary acceptable diluent, carrier or excipient therefore.

21. A method of treating surface wounds in animals, including humans, which method includes administering to a patient to be treated, a pharmacologically effective amount of a pharmaceutical or veterinary composition prepared by the process according to claim 20.

22. A process for preparing a pharmaceutical or veterinary composition for the treatment of surface wounds, said process includes:
(a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
filtering the milk product to remove solid material therefrom;
adjusting the pH of the resulting ultrafiltrate to between approximately 6.5 and 8.0;
equilibrating an agarose-based cation exchange resin with an equilibration buffer to provide a cation exchange resin suitable for adsorbing basic protein;
applying the pH adjusted ultrafiltrate to the equilibrated cation exchange resin;
eluting the cation exchange resin with a buffer suitable for such eluting and recovering an eluate comprising said growth factors in a fraction having a high molecular weight;
filtering the eluate to reduce the salt content thereof;
concentrating the filtered eluate to obtain the milk protein mixture enriched in growth promoting activity and having the ability to stimulate proliferation of rat myoblasts;
(b) providing a source of acid;
(c) providing a pharmaceutically or veterinary acceptable diluent, carrier or excipient therefore; and
(d) subjecting the milk protein mixture to transient acidification utilizing the acid source for a period sufficient to enhance the growth promoting activity of growth factors in the milk protein mixture to obtain an acidified growth promoting extract; with a cell growth promoting activity that is enhanced as compared with the cell growth promoting activity of the milk protein mixture provided in step (a); and
(e) combining said acidified growth promoting extract with the pharmaceutically or veterinary acceptable diluent, carrier or excipient therefore.

23. A method of treating surface wounds in animals, including humans, which method includes administering to a patient to be treated, an effective amount of a pharmaceutical or veterinary composition prepared by the process according to claim 22.

24. A process for preparing a pharmaceutical or veterinary composition for the treatment of gastro-intestinal injuries, diseases or ulcers, said process includes:
(a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
1) filtering the milk product to remove solid material therefrom:
2) contacting the product thereof with an equilibrated cation exchange resin to adsorb the more basic components of the mixture and then eluting the resin with a buffer solution and recovering an eluate comprising said growth factors in a fraction having a high molecular weight;
3) diafiltration of the eluate against water; and
4) concentrating the filtered eluate to obtain the milk protein mixture enriched in growth promoting activity and having the ability to stimulate proliferation of rat myoblasts; and
(b) providing a source of acid;
(c) providing a pharmaceutically or veterinary acceptable diluent, carrier or excipient therefore;
(d) subjecting the milk protein mixture to transient acidification utilizing the acid source to obtain an acidified growth promoting extract with a cell growth promoting activity that is enhanced as compared with the cell growth promoting activity of the milk protein mixture provided in step (a); and
(e) combining said acidified growth promoting extract with the pharmaceutically or veterinary acceptable diluent, carrier or excipient therefore.

25. A method of treating gastrointestinal injuries, diseases or ulcers, which method includes administering to the patient to be treated an pharmacologically effective amount of a pharmaceutical or veterinary composition prepared by the process according to claim 24.

26. A process for preparing a pharmaceutical or veterinary composition for the treatment of gastro-intestinal injuries, diseases or ulcers, said process includes:
(a) providing a milk protein mixture from a milk product selected from the group consisting of cheese whey, skim milk, and casein whey, the milk protein mixture comprising growth factors having a basic to approximately neutral isoelectric point, being enriched in growth promoting activity, and having the ability to stimulate proliferation of rat myoblasts, the milk protein mixture being prepared by:
filtering the milk product to remove solid material therefrom;
adjusting the pH of the resulting ultrafiltrate to between approximately 6.5 and 8.0;
equilibrating an agarose-based cation exchange resin with an equilibration buffer to provide a cation exchange resin suitable for adsorbing basic protein;
applying the pH adjusted ultrafiltrate to the equilibrated cation exchange resin;
eluting the cation exchange resin with a buffer suitable for such eluting and recovering an eluate comprising said growth factors in a fraction having a high molecular weight;
filtering the eluate to reduce the salt content thereof;
concentrating the filtered eluate to obtain the milk protein mixture enriched in growth promoting activity and having the ability to stimulate proliferation of rat myoblasts;
(b) providing a source of acid;
(c) providing a pharmaceutically or veterinary acceptable diluent, carrier or excipient therefore; and
(d) subjecting the milk protein mixture to transient acidification utilizing the acid source for a period sufficient to enhance the growth promoting activity of growth factors in the milk protein mixture to obtain an acidified growth promoting extract with a cell growth promoting activity that is enhanced as compared with the cell growth promoting activity of the milk protein mixture provided in step (a); and
(e) combining said acidified growth promoting extract with the pharmaceutically or veterinary acceptable diluent, carrier or excipient therefore.

27. A method of treating gastrointestinal injuries, diseases or ulcers, which method includes administering to the patient to be treated an pharmacologically effective amount of a pharmaceutical or veterinary composition prepared by the process according to claim 26.

* * * * *